United States Patent
Andreas et al.

(10) Patent No.: US 7,323,006 B2
(45) Date of Patent: Jan. 29, 2008

(54) RAPID EXCHANGE INTERVENTIONAL DEVICES AND METHODS

(75) Inventors: Bernard Andreas, Redwood City, CA (US); Jeffry J. Grainger, Portola Valley, CA (US)

(73) Assignee: Xtent, Inc., Menlo Park, CA (US)

( * ) Notice: Subject to any disclaimer, the term of this patent is extended or adjusted under 35 U.S.C. 154(b) by 459 days.

(21) Appl. No.: 10/814,581

(22) Filed: Mar. 30, 2004

(65) Prior Publication Data

US 2005/0222603 A1    Oct. 6, 2005

(51) Int. Cl.
  *A61F 2/06*    (2006.01)
(52) U.S. Cl. .................... 623/1.11; 600/585
(58) Field of Classification Search ........... 604/164.13, 604/278, 167.06
  See application file for complete search history.

(56) References Cited

U.S. PATENT DOCUMENTS

| | | | |
|---|---|---|---|
| 4,762,129 A | 8/1988 | Bonzel | |
| 4,988,356 A | 1/1991 | Crittenden et al. | |
| 5,040,548 A | 8/1991 | Yock | |
| 5,135,535 A | 8/1992 | Kramer | |
| 5,300,085 A | 4/1994 | Yock | |
| 5,334,187 A | 8/1994 | Fischell et al. | |
| 5,490,837 A * | 2/1996 | Blaeser et al. ......... | 604/103.11 |
| 5,496,346 A | 3/1996 | Horzewski et al. | |
| 5,501,227 A | 3/1996 | Yock | |
| 5,980,484 A | 11/1999 | Ressemann et al. | |
| 5,980,486 A | 11/1999 | Enger | |
| 6,004,328 A * | 12/1999 | Solar .......................... | 623/1.11 |
| 6,007,517 A | 12/1999 | Anderson | |
| 6,056,722 A | 5/2000 | Jayaraman | |
| RE36,857 E | 9/2000 | Euteneuer et al. | |
| 6,165,167 A | 12/2000 | Delaloye | |
| 6,196,995 B1 | 3/2001 | Fagan | |
| 6,379,365 B1 * | 4/2002 | Diaz .......................... | 606/108 |
| 6,488,694 B1 | 12/2002 | Lau et al. | |
| 6,527,789 B1 | 3/2003 | Lau et al. | |
| 6,569,180 B1 * | 5/2003 | Sirhan et al. ............... | 606/194 |
| 6,575,993 B1 | 6/2003 | Yock | |
| 6,579,305 B1 * | 6/2003 | Lashinski ................... | 623/1.11 |
| 6,592,549 B2 | 7/2003 | Gerdts et al. | |
| 6,605,062 B1 | 8/2003 | Hurley et al. | |
| 6,605,109 B2 * | 8/2003 | Fiedler ..................... | 623/1.12 |
| 6,679,909 B2 | 1/2004 | McIntosh et al. | |

(Continued)

FOREIGN PATENT DOCUMENTS

EP    203945 B2    12/1986

(Continued)

*Primary Examiner*—Glenn K. Dawson
(74) *Attorney, Agent, or Firm*—Townsend and Townsend and Crew LLP; J. Grainger, Esq.

(57) ABSTRACT

Wire-guided interventional devices and methods are provided which enable faster and easier catheter exchanges. The interventional devices include a catheter shaft and a guidewire tube wherein the catheter shaft and the guidewire tube each have a length sufficient to extend to the vascular penetration when the interventional device is positioned at the treatment site. In some embodiments, a collar is disposed around the catheter shaft and guidewire tube that automatically inserts or removes the guidewire from the guidewire tube or automatically collapses or extends the guidewire tube as the catheter is introduced or withdrawn.

29 Claims, 8 Drawing Sheets

U.S. PATENT DOCUMENTS

| | | |
|---|---|---|
| 6,692,465 B2 | 2/2004 | Kramer |
| 6,723,071 B2 | 4/2004 | Gerdts et al. |
| 6,800,065 B2 * | 10/2004 | Clarke et al. ............ 604/96.01 |
| 6,893,417 B2 * | 5/2005 | Gribbons et al. ...... 604/103.04 |
| 2003/0199821 A1 | 10/2003 | Gerdts et al. |

FOREIGN PATENT DOCUMENTS

| | | |
|---|---|---|
| EP | 274129 B1 | 7/1988 |
| EP | 282143 B1 | 9/1988 |

* cited by examiner

RAPID EXCHANGE INTERVENTIONAL DEVICES AND METHODS

BACKGROUND OF THE INVENTION

The use of wire-guided catheter interventions for diagnosis and treatment of disease is increasing dramatically. Such interventions are employed in the arterial and venous vasculature, in the heart, kidneys, liver, and other organs, in the stomach, intestines, and urinary tract, in the trachea and lungs, in the uterus, ovaries and fallopian tubes, and elsewhere. As new miniaturized and less-invasive technologies are developed, the challenge becomes one of gaining access to the anatomical regions that could benefit from new forms of diagnosis and treatment. Wire-guided catheters provide a proven, minimally-invasive approach to reaching remote regions of the body and performing diagnostic and treatment procedures with precision, safety, and reliability.

A particularly well-known use of wire-guided catheters is for the treatment of coronary artery disease. In coronary artery disease, one or more coronary arteries becomes partially or fully occluded by the build-up of stenotic plaque, slowing or completely blocking blood flow to the heart muscle. If the heart muscle is deprived of blood, a myocardial infarction results, destroying heart muscle tissue and potentially leading to death.

Various coronary interventions have been developed to treat coronary artery disease. Angioplasty involves the use of a balloon catheter that is introduced into a peripheral artery and advanced over a guidewire to the target coronary artery. A balloon on the end of the catheter is expanded within the stenotic lesion to widen the coronary lumen and restore patency. It has been found, however, that in more than 30% of cases, restenosis occurs to again block the artery 6-12 months after angioplasty. To address this issue, coronary stents have been developed, tubular wire mesh scaffolds that are delivered via catheter to the coronary lesion and expanded into engagement with the wall of the artery to maintain its patency. While bare metal stents also experience a significant incidence of restenosis, the use of drug-coated stents in recent years has demonstrated a dramatic reduction in restenosis rates. Angioplasty and stents are also utilized in other vascular regions, including the femoral, iliac, carotid, and other peripheral arteries, as well as in the venous system.

Guidewires are commonly used to facilitate delivery of angioplasty and stent delivery catheters through the vasculature to the target lesion to be treated. Such guidewires are inserted through a vascular access site, usually a puncture, incision or other penetration in a peripheral artery such as a femoral or iliac artery. A guiding catheter is often used to cannulate the ostium of the left or right coronary artery, and the guidewire and other catheters are then introduced through the guiding catheter. Such guiding catheters typically include a hemostasis valve to facilitate insertion and withdrawal of devices while providing a hemostatic seal around the periphery of such devices to minimize blood loss.

The proximal end of the guidewire outside the body is threaded through a guidewire lumen in the delivery catheter to be used. If the catheter is an "over-the-wire" type, the guidewire lumen typically extends through the catheter shaft from the distal tip of the catheter to its proximal end. The disadvantage of such designs is that the guidewire must be very long in order to extend entirely through the catheter while the distal end of the guidewire remains positioned at the target lesion. Further, the process of exchanging catheters (withdrawing a first catheter from the guidewire and replacing it with a second catheter) is challenging and time-consuming with over-the-wire designs because in the region of the vascular penetration, the guidewire is covered by the catheter being withdrawn until the catheter has been completely removed from the patient, preventing the physician from keeping hold of the guidewire and requiring the use of an assistant to hold the proximal end of the guidewire some distance from the patient.

In response to these challenges with over-the-wire catheters, various types of "rapid exchange" catheters have been developed. In one design, the catheter has a shortened guidewire lumen that extends from the distal tip of the catheter to a point a short distance proximal to the balloon, stent, or other interventional element. This permits the use of a substantially shorter guidewire because the proximal end of the guidewire can emerge from the guidewire lumen a relatively short distance from the distal end of the catheter. This design facilitates faster and easier catheter exchanges because the shorter wire is easier to manage and keep sterile, and the shorter guidewire lumen allows the physician to maintain hold on the guidewire as the first catheter is withdrawn and a second is replaced. Examples are seen in U.S. Pat. Nos. 4,762,129, 5,980,484, 6,165,167, 5,496,346, 5,980,486, and 5,040,548.

In an alternative design, a guidewire lumen is provided through the catheter shaft from its distal end to the proximal end or to a point a substantial distance from the distal end, as in over-the-wire designs. However, the catheter wall has a longitudinal slit in communication with the guidewire lumen over all or a portion of its length. This allows the proximal end of the guidewire to exit the guidewire lumen through the slit at any of various locations along the length of the catheter. In some designs, the guidewire is threaded through a zipper-like device that slides along the longitudinal slit to insert or remove the guidewire from the guidewire lumen. Examples are seen in U.S. Pat. Nos. 6,527,789, 5,334,187, 6,692,465, Re 36,587, and 4,988,356.

While rapid exchange catheters have many advantages over over-the-wire designs, current rapid exchange catheters suffer from certain drawbacks. For example, in those rapid exchange designs having a shortened guidewire lumen, the guidewire is exposed outside of the catheter and runs alongside the catheter for a substantial distance within the vessel from the vascular access site to the point at which the guidewire enters the guidewire lumen. In "zipper" type designs, while the guidewire may be enclosed within the catheter in the vessel, the guidewire lumen is integral to the catheter shaft between the distal and proximal ends thereof, increasing its profile and stiffness.

For these and other reasons, improved interventional devices with rapid exchange capabilities are desired. The interventional devices should provide the benefits of conventional rapid exchange catheters, including allowing the use of shorter guidewires and facilitating catheter exchanges by allowing the physician to continually hold and manipulate the guidewire from a position near the vascular access site as a catheter is withdrawn and replaced. Further, the interventional devices should keep the guidewire fully enclosed in the guidewire lumen within the vessel between the vascular access site and the catheter balloon, stent, or other interventional element on the catheter. Additionally, the interventional devices should have a shaft of minimal profile and stiffness in its proximal extremity.

BRIEF SUMMARY OF THE INVENTION

The present invention provides interventional devices and methods for performing vascular interventions that facilitate the use of shorter guidewires, and more rapid exchange of catheters, and provide other advantages over conventional rapid exchange catheters. While the devices and methods of the invention are described primarily in the context of interventions in the arterial system, and particularly in the coronary arteries, the invention will find use in a variety of interventional devices used in various anatomical regions, including peripheral arteries, carotid arteries, veins and vein grafts, vascular grafts, organs such as the heart, liver, and kidneys, intestinal and urinary vessels, the lungs, the uterus, ovaries and fallopian tubes, and other regions in which wire-guided devices are utilized. Such device include balloon catheters for angioplasty, vascular occlusion, valvuloplasty, and other purposes, stent delivery catheters, angiography catheters, intravascular ultrasound devices, drug delivery catheters, endoscopes, bronchoscopes, and other visualization devices, RF mapping and ablation catheters, valve replacement and repair catheters, catheters for delivery of implantable devices, defect repair catheters, and other devices.

In a first aspect, the invention provides an interventional device for introduction through a vascular penetration to a treatment site in a vessel comprising a catheter shaft having a proximal extremity, a distal extremity and an interventional element coupled to the distal extremity; and a guidewire tube having a proximal end, a distal end and a guidewire lumen therebetween configured to slidably receive a guidewire, the distal end being coupled to the distal extremity of the catheter shaft and the proximal end being separate from the catheter shaft; wherein the proximal extremity of the catheter shaft and the guidewire tube each have a length sufficient to extend to the vascular penetration when the interventional device is positioned at the treatment site.

In a further aspect of the invention, the interventional device includes a collar positionable in the vascular penetration and having at least one passage therein configured to slidably receive the proximal extremity of the catheter shaft and the guidewire without substantial leakage of blood therethrough. The collar is positionable through a hemostatic device in the vascular penetration, the collar having an exterior surface configured to seal within the hemostatic device. The hemostatic device may comprise a rotating hemostasis valve (RHV) or other suitable device for introducing catheters into a vessel with minimal leakage of blood. The collar may further include a seal in communication with the at least one passage for inhibiting leakage of blood around the proximal extremity. In some embodiments, the collar comprises a first passage for receiving the catheter shaft and a second passage for receiving the guidewire tube. In other embodiments, a single passage is provided that receives both the catheter shaft and the guidewire tube.

In another aspect of the invention, the guidewire tube comprises a slit disposed longitudinally therein from a distal point less than about 50 cm from the distal end to a proximal point at least about one-half the length of the guidewire tube from the distal end. The proximal point is usually within about 20 cm from the proximal end of the guidewire tube and may be at the proximal end itself. The interventional device may further include a wire guide positionable through the slit and operative upon the guidewire such that the guidewire is disposed in the guidewire lumen distal to the wire guide and disposed outside the guidewire lumen proximal to the wire guide. The wire guide may be coupled to a collar having at least one passage configured to slidably receive the proximal extremity of the catheter shaft and the guidewire tube. The wire guide preferably comprises a distal opening, a proximal opening, and a guide passage therebetween, the distal opening being aligned with the guidewire lumen and the proximal opening being outside the guidewire tube when the wire guide is positioned through the slit. The wire guide may further have a rounded or tapered distal edge configured to spread the slit in the guidewire tube.

In still another aspect of the invention, the guidewire tube is collapsible from an extended length to a collapsed length. In exemplary embodiments, the extended length is at least about 140 cm and the collapsed length is no more than about 30 cm. In these embodiments, the guidewire tube may have any of various collapsible and extendable structures, including an accordion-like wall with a zig-zag cross-section. The guidewire tube may also have a series of generally conical segments connected by hinges, whereby adjacent conical segments are pivotable toward and away from each other about the hinges. The conical or dome-shaped segments may also be configured to nest within one another in the collapsed configuration. Preferably, a collar is provided having at least one passage configured to slidably receive the proximal extremity of the catheter shaft. The proximal end of the guidewire tube is coupled to the collar such that moving the catheter shaft relative to the collar extends or retracts the guidewire tube.

In preferred embodiments, the interventional element comprises a stent. The stent may have a plurality of stent segments. The interventional device may also include a sheath slidably disposed over the stent segments. The sheath may be selectively positioned to deploy a first selected number of stent segments from the catheter shaft while retaining a second selected number of stent segments on the catheter shaft. The interventional element may also comprise an expandable member such as a balloon. Again, a sheath may be slidably disposed over the balloon and selectively positioned to expand a first portion of the balloon while constraining a second portion of the balloon. In some embodiments, the guidewire tube couples with the catheter shaft proximal to the interventional element and extends to a point distal to the interventional element.

The invention further provides methods of performing diagnostic and therapeutic interventions using wire-guided devices. In a first aspect, a method of performing an intervention at a treatment site through a vascular penetration in a vessel comprises providing an interventional device having a catheter shaft, an interventional element coupled to a distal extremity of the catheter shaft, and a guidewire tube having a distal portion coupled to the distal extremity of the catheter shaft and a proximal portion separate from the catheter shaft; placing a distal end of a guidewire through the vascular penetration into the vessel; inserting a proximal end of the guidewire through at least a portion of the guidewire tube; positioning the interventional device through the vascular penetration; and advancing the interventional device through the vessel to position the interventional element at the treatment site, wherein the guidewire is disposed within the guidewire tube between the vascular penetration and the interventional element when the interventional element is at the treatment site. In a preferred aspect, as the interventional device is advanced into the vessel, the guidewire exits the guidewire tube at locations progressively further from the interventional element as the interventional device is inserted. Similarly, when the interventional device is withdrawn, the guidewire exits the guidewire tube at locations progressively closer to the interventional element at the device is withdrawn.

In a further aspect of the method, the guidewire extends out of a slit in a wall of the guidewire tube. The slit may extend from a point no more than about 50 cm proximal to the interventional element to a point at or near the vascular penetration when the interventional element is at the treatment site.

The method may further include positioning a collar in the vascular penetration, the collar being slidably disposed over catheter shaft and the guidewire tube, wherein advancing the interventional device comprises moving the catheter shaft and guidewire tube relative to the collar. The collar may have a wire guide that extends through the slit in the guidewire tube, and wherein moving the guidewire tube relative to the collar guides the guidewire into or out of the guidewire tube. Usually, a hemostasis device is placed in the vascular penetration, and the collar is positioned in the hemostasis device. The hemostasis device provides a hemostatic seal between the hemostasis device and the collar. The interventional device may also include a seal in the collar to inhibit blood leakage from the vessel around the catheter shaft and guidewire tube.

In another aspect of the method, the guidewire tube is collapsible from an extended length to a collapsed length, wherein the guidewire tube has the collapsed length before the interventional device is inserted into the vessel and has the extended length when the interventional element is at the treatment site. The interventional device may include a collar slidable relative to the catheter shaft and coupled to the guidewire tube. In this way, advancing the interventional device relative to the collar extends the length of the guidewire tube.

In preferred embodiments, the interventional element comprises a stent, and the method further comprising deploying the stent at the treatment site. In these embodiments, the interventional element preferably comprises a plurality of stent segments, the method further comprising deploying a first selected number of the stent segments at the treatment site while retaining a second selected number of stent segments on the catheter shaft. The interventional element may also comprise a balloon, wherein the method further comprising expanding the balloon at the treatment site. Preferably, a first selected portion of the balloon is expanded while constraining a second selected portion of the balloon.

In a further aspect of the invention, a method of performing an intervention at a treatment site through a vascular penetration in a vessel comprises providing an interventional device having a catheter shaft, an interventional element coupled to a distal extremity of the catheter shaft, and a guidewire tube having a distal portion coupled to the distal extremity of the catheter shaft; placing a distal end of a guidewire through the vascular penetration into the vessel; positioning a proximal end of the guidewire through at least a portion of the guidewire tube such that the proximal end of the guidewire exits the guidewire tube at a point closer to a distal end of the interventional device than to a proximal end of the interventional device; positioning the interventional device through the vascular penetration; and advancing the interventional device through the vessel to position the interventional element at the treatment site, wherein the guidewire exits the guidewire tube closer to the proximal end of the interventional device than to the distal end of the interventional device when the interventional element is at the treatment site.

Further aspects of the nature and advantages of the invention will become apparent from the following detailed description when taken in conjunction with the drawings.

DETAILED DESCRIPTION OF THE INVENTION

Figure 1:
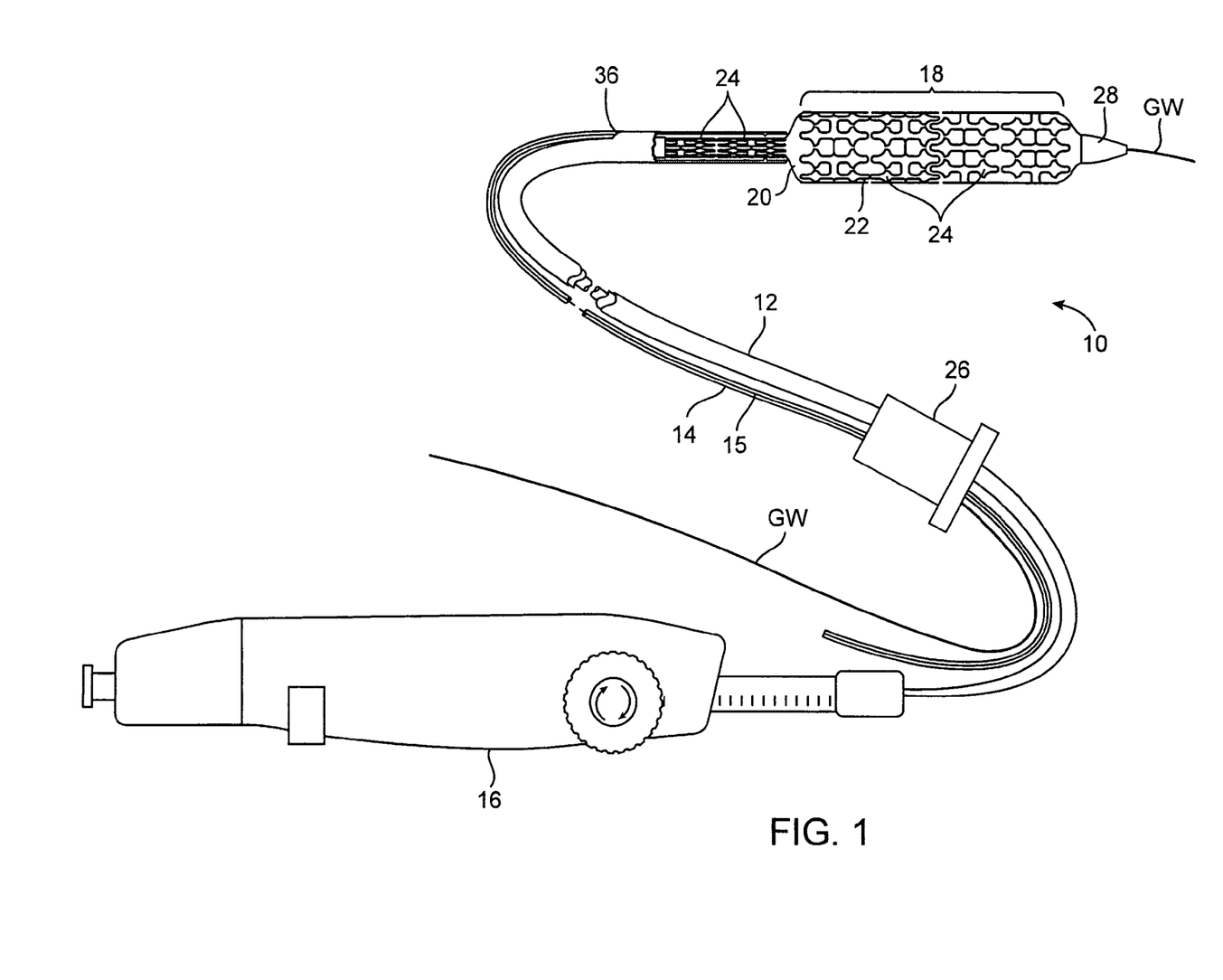
FIG. 1 is a side elevational view of a stent delivery catheter according the invention.

Referring to FIG. 1, a first embodiment of an interventional device according to the invention will be described. In this embodiment, the interventional device is a stent delivery catheter 10 having a catheter body 12, a guidewire tube 14 with a longitudinal slit 15, a handle 16, and an interventional element 18. Interventional element 18 comprises an expandable balloon 20 coupled to catheter body 12, and one or more stents 22 positioned over balloon 20 for expansion therewith. In a preferred embodiment, each stent 22 comprises a plurality of separate or separable stent segments 24, some of which are shown expanded on balloon 20 while others are retained within catheter body 12. Catheter body 12 and guidewire tube 14 extend through a collar 26 and are slidable relative thereto. A guidewire GW extends slidably through guidewire tube 14 between a nosecone 28 at the distal end of catheter body 12 and collar 26.

Delivery catheter 10 has dimensions suitable for use in the anatomical region to be treated. In one embodiment suitable for stent delivery to the coronary arteries, catheter body 12 has a length of about 100-200 cm and an outer diameter of about 0.1-0.5 cm. Balloon 20 may have a length of about 2-12 cm and an expanded diameter of about 2-10 mm. Balloon 20 may also be tapered, stepped, or have other geometry suitable for the target region. Stent segments are preferably about 2-10 mm in length and have an unexpanded diameter of about 0.5-2 mm. Guidewire tube 14 has an outer diameter of about 0.3-0.6 mm, an inner diameter of about 0.2-0.5 mm, and a length approximately the same as that of catheter body 12.

Figure 2A:
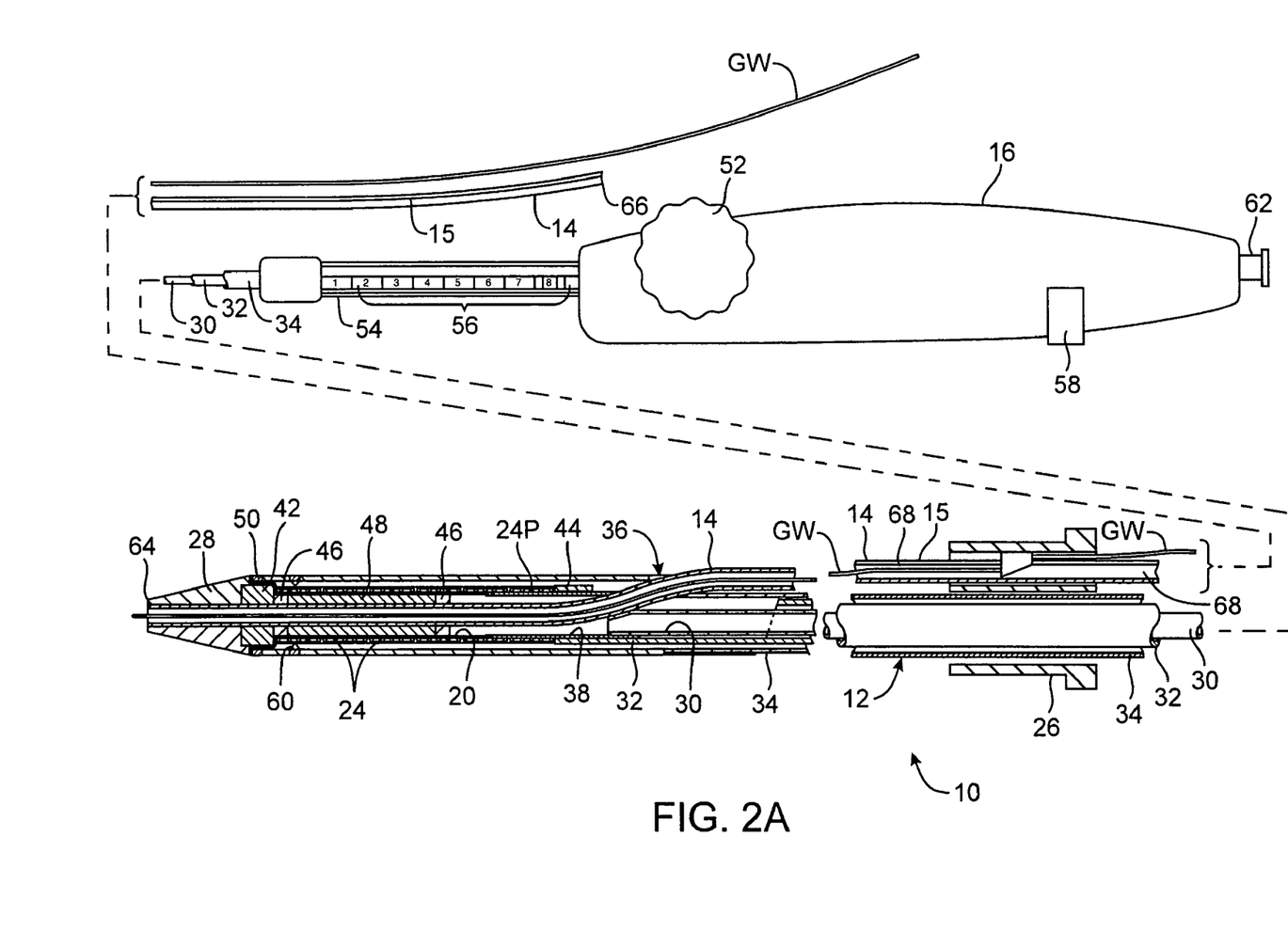
FIGS. 2A-2B are side partial cross-sectional views of the stent delivery catheter of FIG. 1 with the balloon deflated and inflated, respectively.
Figure 2B:
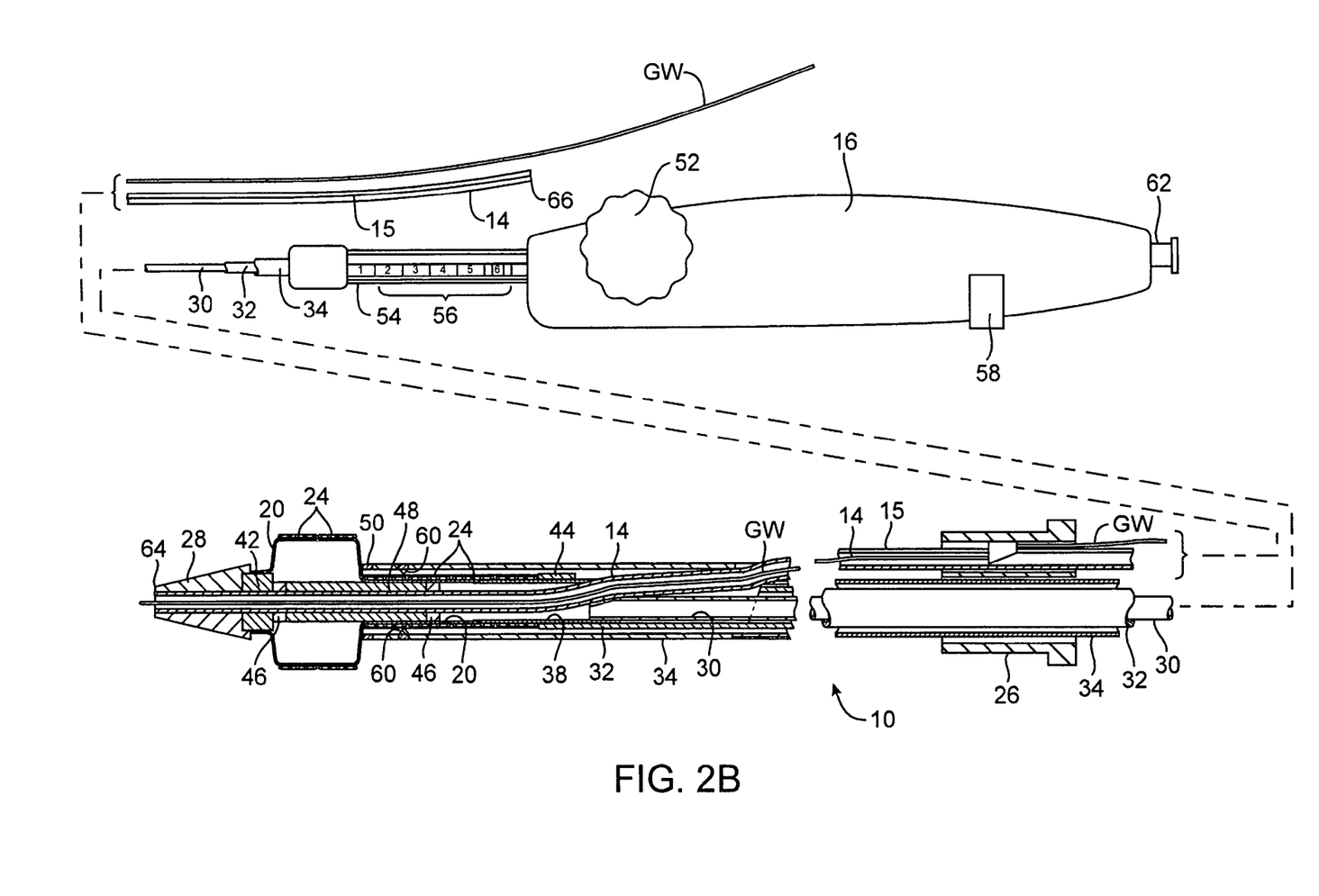

Catheter body 12 includes, as further illustrated in FIGS. 2A-2B, a tubular inflation shaft 30, a tubular pusher 32 slidably disposed over inflation shaft 30, and a tubular sheath 34 slidably disposed over pusher 32. Guidewire tube 14 extends slidably through a port 36 in sheath 34 and passes through balloon 20 and nosecone 28, to which it is attached. Balloon 20 has a proximal balloon leg 38 fixed at its proximal end to guidewire tube 14 and inflation shaft 30, and at its distal end to a stent stop 42 fixed to guidewire tube 14 and/or nosecone 28. Stent segments 24 are slidably disposed over balloon leg 38 and balloon 20. An endring 44 attached to pusher 32 engages the proximal-most stent segment 24P and facilitates advancing the line of stent segments 24 distally relative to balloon 20. A plurality of radiopaque markers 46 are fixed to guidewire tube 14 within balloon 20 to facilitate positioning of catheter 20 using fluoroscopy. A build-up 48 is optionally provided around guidewire tube 14 within balloon 20 to enhance frictional engagement between balloon 20 and stent segments 24 when the balloon is deflated. Sheath 34 has a metallic reinforcing ring 50 at its distal end that resists expansion when balloon 20 is inflated. Other aspects of the construction and operation of delivery catheter 10 are described in copending application Ser. No. 10/637,713, filed Aug. 8, 2003, which is incorporated herein by reference.

When stent segments 24 are to be deployed, sheath 34 is retracted relative to balloon 20 as illustrated in FIG. 2B. A knob 52 on handle 16 is coupled to a sheath housing 54 which is attached to sheath 34, whereby knob 52 is rotated to retract sheath 34. Indicia 56 are provided on sheath housing 54 to indicate the distance that the sheath has been retracted and/or the number of stent segments 24 exposed on balloon 20 distally of sheath 24. Other aspects of handle 16 are described in copending application Ser. No. 10/746,466, filed Dec. 23, 2003, entitled "Devices and Methods for Controlling and Indicating the Length of an Interventional Element," which is incorporated herein by reference.

As sheath 34 is retracted, pusher 32 may be either in a locked or unlocked mode. A pivotable switch 58 on handle 16 is coupled to pusher 32 and is movable between a first position in which pusher 32 is decoupled from sheath 34 and held in a fixed position relative to balloon 20 (locked), and a second position in which pusher 32 is coupled so as to move with sheath 34 (unlocked). In the locked mode, pusher 32 exerts force distally against stent segments 24 as sheath 34 is retracted, maintaining their position on balloon 20. This allows the user to expose the desired number of stent segments 24 that are to be deployed according to the length of the lesion being treated. In the unlocked mode, pusher 32 is allowed to move proximally relative to balloon 20 as sheath 34 is retracted. An annular ridge 60 on the inner wall of sheath 34 near its distal end is configured to engage stent segments 24 whereby, in the absence of force exerted by pusher 32, stent segments 24 slide proximally with sheath 34 as the sheath is retracted. This may be used for two purposes: First, it allows the user to expose a desired length of balloon 20 without any of stent segments 24 thereon to perform pre- or post-dilatation at the treatment site. Second, it allows the user to create a small gap separating the exposed stent segments 24 to be deployed from those retained within sheath 34 so that upon balloon expansion, the segments 24 remaining in sheath 34 are not expanded or deformed.

When the desired length of balloon 20 and/or number of stent segments 24 have been exposed distally of sheath 34, balloon 20 may be expanded by delivering an inflation fluid through inflation port 62 on handle 16. Inflation port 62 communicates with inflation shaft 30 to deliver the inflation fluid to the interior of balloon 20. Stent segments 24 are preferably a malleable metal such as stainless steel, cobalt chromium, MP35N or other suitable material that plastically deforms as balloon 20 is inflated to maintain stent segments 24 in an expanded tubular configuration. Self-expanding stent materials including shape memory or superelastic alloys such as Nitinol as well as various polymers may also be utilized. Biodegradable polymer stents, stent-grafts, covered stents, and various other stent-like structures may also be deployed using catheter 20. Any of these various types of stents may be impregnated, coated, or otherwise combined with polymers, ceramics, metals, proteins, and/or therapeutic agents to enhance their effectiveness and/or to reduce restenosis. In a preferred embodiment, stent segments 24 are coated first with a polymeric undercoat or primer such as parylene then with a biodegradable polymeric coating comprising a poly-lactic-acid mixed or combined with an anti-restenosis agent such as taxol, rapamycin, or analog of either. Other aspects of stent segments 24 are described in copending application Ser. No. 10/738,666, filed Dec. 16, 2003, entitled "Multiple Independent Nested Stent Structures and Methods for Their Preparation and Deployment," which is incorporated herein by reference.

Longitudinal slit 15 in guidewire tube 14 extends from the proximal end 66 of guidewire tube 14 to a point in the distal half of catheter 20, preferably near balloon 20. While slit 15 could extend through balloon 20 all the way to the distal tip of guidewire tube 14, in a preferred embodiment, slit 15 terminates at a point about 20-50 cm proximally of the distal tip 64 of nosecone 28, and about 10-40 cm proximally of the proximal end of the expandable portion of balloon 20. The distal end of slit 15 may be disposed either within or outside of sheath 34, but is preferably outside of sheath 34, e.g. about 0.1-10 cm proximal to port 36 when sheath 34 is in a fully distal position. Slit 15 preferably extends all the way to the proximal end 66 of guidewire tube 14, although slit 15 may alternatively terminate some distance distally of proximal end 66, but preferably no more than about 30 cm therefrom and usually no more than one-half the distance to the distal tip 64 from proximal end 66.

Figure 3A:
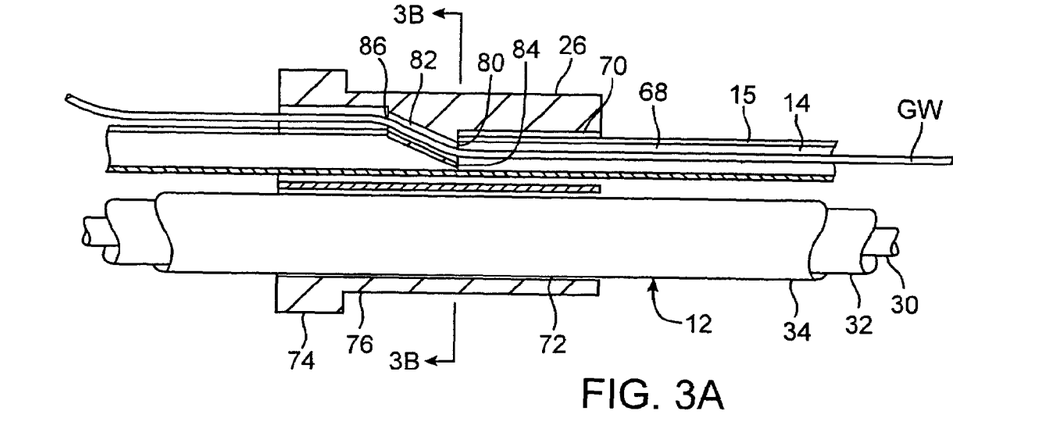
FIG. 3A is a side cross-sectional view of a collar in the stent delivery catheter of FIG. 1.
Figure 3B:
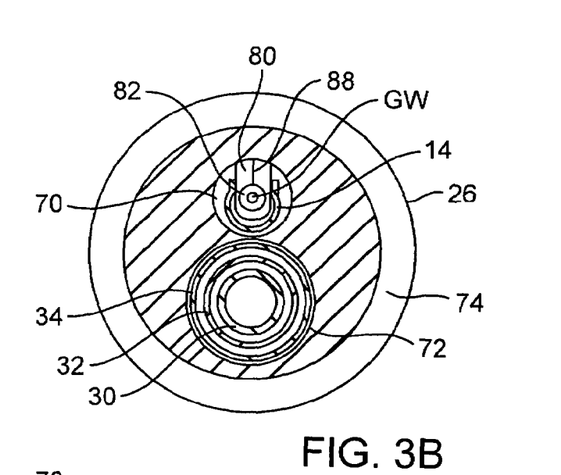
FIG. 3B is a transverse cross-section of the collar of FIG. 3A.
Figure 3C:
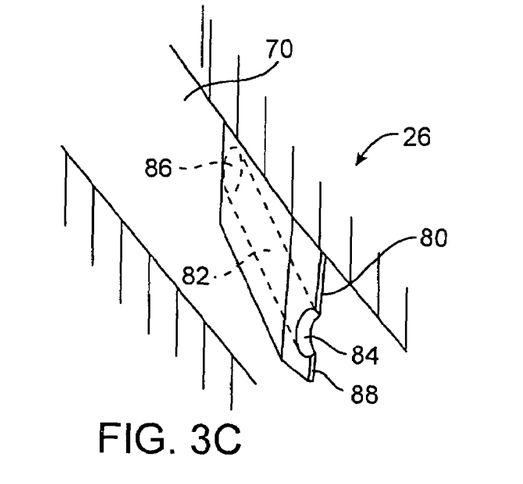
FIG. 3C is an oblique partial cross sectional view of the collar of FIG. 3A.

As illustrated in FIGS. 3A-3C, collar 26 has a first channel 70 configured to receive guidewire tube 14 and a second channel 72 configured to receive catheter body 12. Preferably, first and second channels 70, 72 are configured to provide a slidable, sealed fit with guidewire tube 14 and catheter body 12 so as to minimize blood leakage therethrough. Optionally, elastomeric seals or valves (not shown) may be provided in one or both of channels 70, 72 to seal against the exterior of guidewire tube 14 and catheter body 12 to further inhibit blood leakage. Collar 26 is configured to be inserted through a rotating hemostasis valve (RHV) of a guiding catheter or other hemostatic device placed in a vascular penetration. A flange 74 is disposed around the proximal end of collar 26 to seat against the RHV and prevent over-insertion. The exterior surface 76 of collar 26 is configured to seal within the RHV to inhibit leakage of blood around collar 26.

A wedge-shaped wire guide 80 extends radially inwardly into first channel 70 and is configured to extend through slit 15 into guidewire tube 14. Wire guide 80 has a passage 82 through which guidewire GW may slide. Passage 82 is disposed at an oblique angle relative to the axial direction such that the distal opening 84 in passage 82 is aligned with guidewire lumen 68, while the proximal opening 86 is radially offset from guidewire lumen 68, outside of guidewire tube 14. In this way, as guidewire tube 14 moves distally relative to collar 26, guidewire GW is guided into guidewire tube 14, while moving guidewire tube proximally relative to collar 26 removes guidewire GW from guidewire tube 14. Thus, guidewire GW is disposed within guidewire tube 14 between collar 26 and distal end 64 of catheter 10, but is outside of guidewire tube 14 between collar 26 and proximal end 66 of guidewire tube 14 (or handle 16). To facilitate sliding movement of wire guide 80 through slit 15, wire guide 80 has a tapered, beveled, or rounded leading edge 88 that helps to engage and widen slit 15.

Figure 4A:
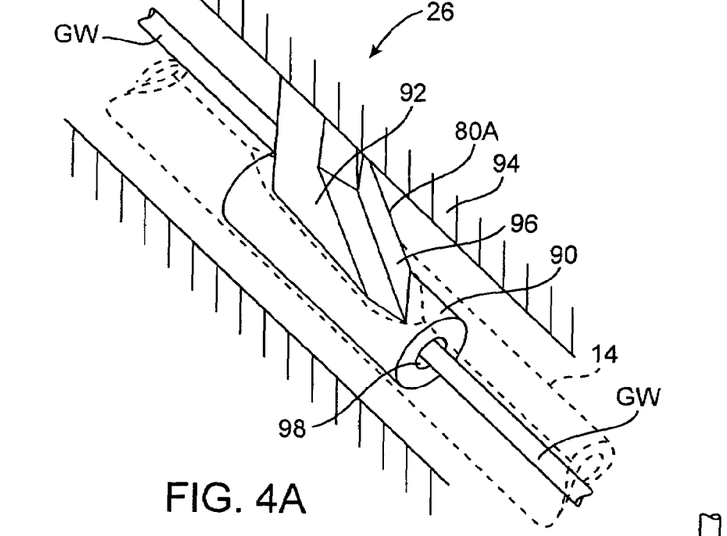
FIG. 4A is an oblique partial cross sectional view of a further embodiment of a collar in a stent delivery catheter according to the invention.
Figure 4B:
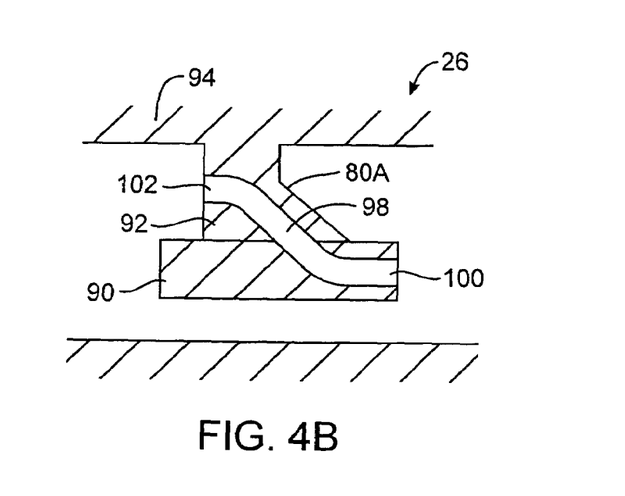
FIG. 4B is a partial side cross sectional view of a wire guide in the collar of FIG. 4A.
Figure 4C:
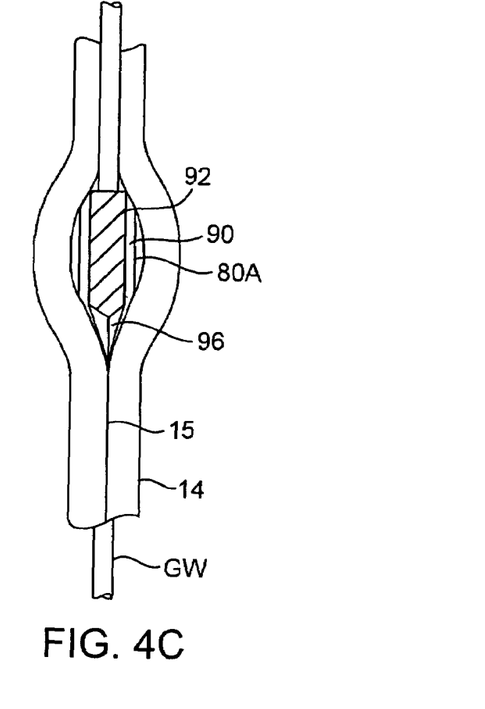
FIG. 4C is a partial top cross sectional view of a wire guide in the collar of FIG. 4A.

A second embodiment of a wire guide 80A in collar 26 is illustrated in FIGS. 4A-4C. Wire guide 80A includes a generally cylindrical bottom tube 90 configured to slide within guidewire lumen 68. Bottom tube 90 may be round, oval, elliptical, disk-shaped or other suitable shape in cross-section, and may have a pointed, conical, bullet-shaped, or rounded leading edge to assist in tracking through guidewire lumen 68. Bottom tube 90 is fixed to a base 92 attached to the wall 94 of collar 26. Base 92 is configured to extend through slit 15 in guidewire tube 14. The leading edge 96 of base 92 may be tapered, peaked, rounded or have other suitable shape to assist in sliding through and spreading slit 15. A passage 98 extends from a distal opening 100 in bottom tube 90 to a proximal opening 102 on the proximal side of base 92. Distal opening is aligned with guidewire lumen 68, while proximal opening 102 is radially offset therefrom so that guidewire GW is guided from being within guidewire lumen 68 distally of wire guide 80A to being outside guidewire lumen 68 proximally of wire guide 80A.

Figure 5A:
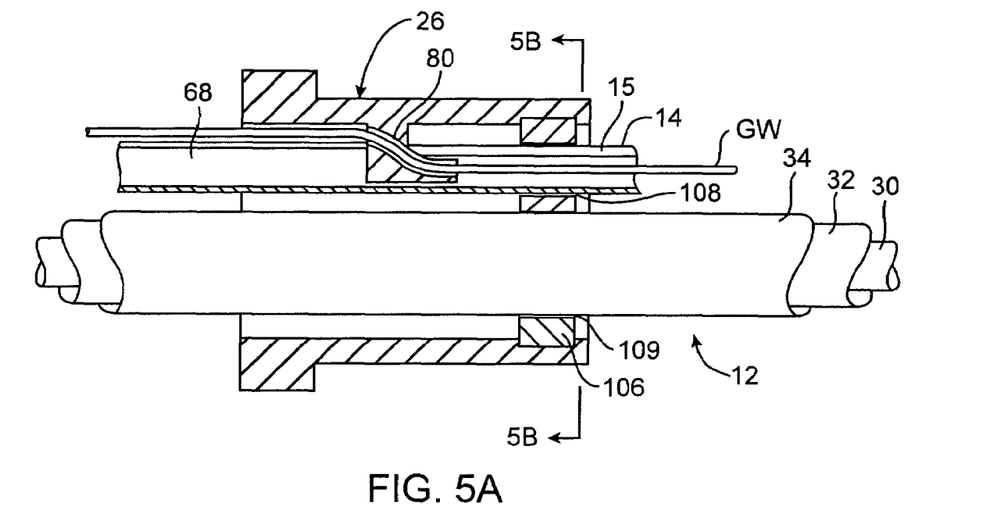
FIG. 5A is a side cross-section of another embodiment of a collar in an interventional catheter according to the invention.
Figure 5B:
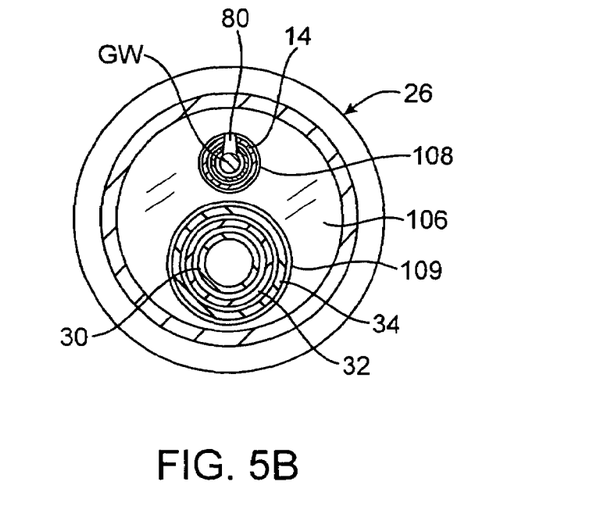
FIG. 5B is a transverse cross-section of the collar of FIG. 5A.

A further embodiment of collar 26 is illustrated in FIGS. 5A-5B. In this embodiment, collar 26 has a single channel 104 extending axially therethrough. Channel 104 is configured to receive both guidewire tube 14 and catheter body 12. A wire guide 80, which may have any of the configurations described above, extends into channel 104 from the wall of collar 26. Wire guide 80 is configured to extend through slit 15 in guidewire tube 14 and guides guidewire GW into and out of guidewire lumen 68 as guidwire tube 14 is moved distally or proximally relative to collar 26. In order to minimize leakage of blood through channel 104, an elastomeric hemostatic seal 106 is mounted within collar 26 across channel 104. Seal 106 has a first hole 108 configured slidably receive and seal against the exterior of guidewire tube 14, and a second hole 109 configured to slidably receive and seal against the exterior of catheter body 12. Seal 106 may be of various elastomeric materials and may have any suitable design to provide hemostatic sealing, including diaphragm, duckbill, slit, flapper, or other type.

Figure 6:
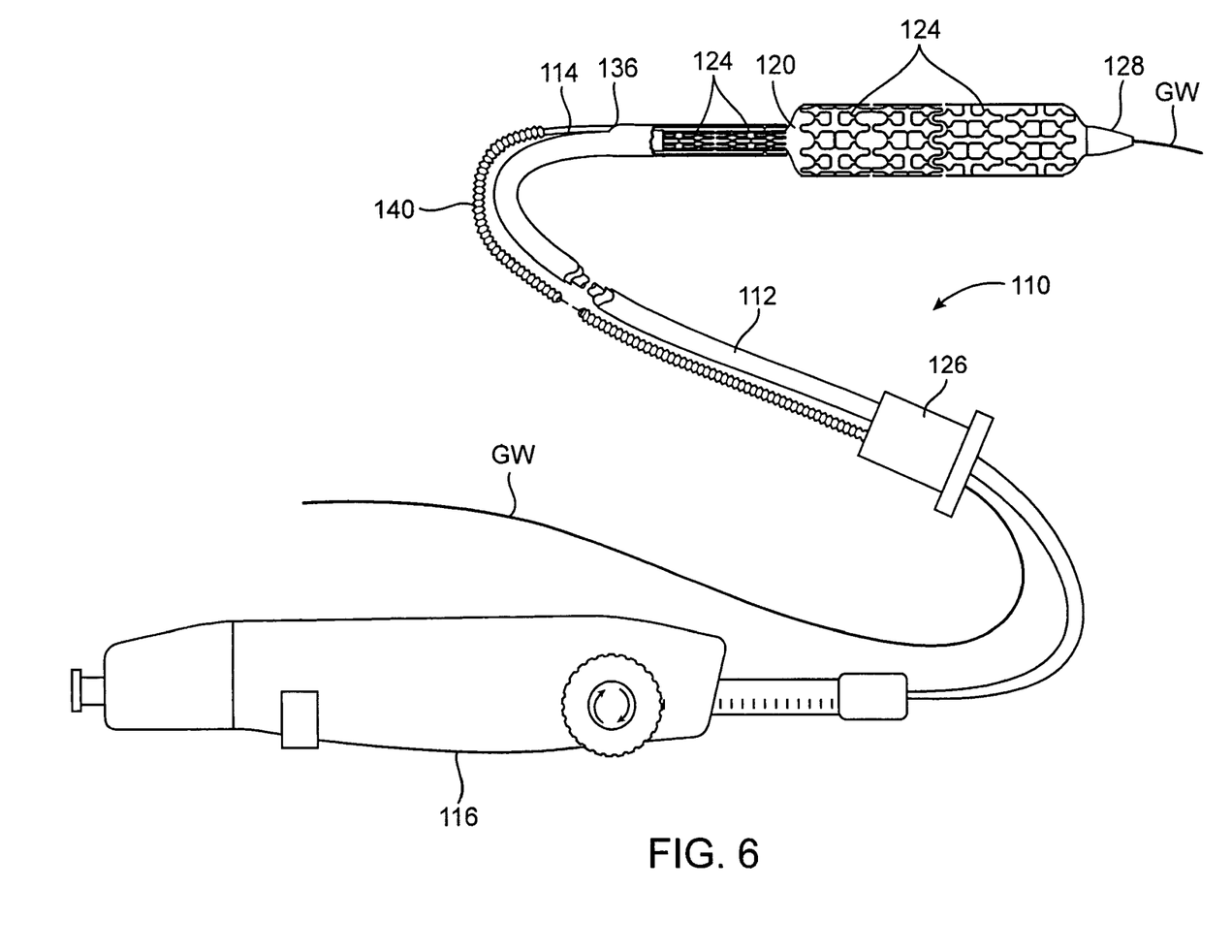
FIG. 6 is a side elevational view of a stent delivery catheter according to the invention in a further embodiment thereof.

Another embodiment of an interventional device according to the invention is illustrated in FIG. 6. In this embodiment, delivery catheter 110 has a catheter body 112, handle 116, balloon 120, stent segments 124, and nosecone 128 constructed as described above in connection with FIGS. 1-2. Guidewire tube 114 extends from nosecone 128 through balloon 120 and out of a port 136 in catheter body 112 as described above. A collar 126 is slidably disposed around guidewire tube 114 and catheter body 112 and is configured to be placed in a vascular penetration or in a hemostasis valve of a guide catheter or other access device.

Unlike previous embodiments, guidewire tube 114 is collapsible from an extended length approximately the same as that of catheter body 112, to a substantially shorter collapsed length, e.g. 5-50 cm, more preferably 10-30 cm. These lengths will of course vary according to the region in which the interventional catheter is to be used, but generally the collapsed length will be less than about 50%, usually about 10%-40%, and preferably less than about 30% of the extended length. In an exemplary configuration, guidewire tube 114 has a collapsible section 140 extending from a point near port 136 proximally to collar 126, to which it is attached. In this way, as catheter body 112 is moved distally relative to collar 126, guidewire tube 114 is extended, while as catheter body 112 is moved proximally relative to collar 126, guidewire tube 114 is collapsed. This effectively makes the point at which guidewire GW exits the guidewire tube movable relative to catheter body 112 from a location near balloon 120 to a location near handle 116 depending upon the distance catheter 110 has been inserted into the vessel. At the same time, from collar 126 all the way to the tip of nosecone 128, guidewire GW is entirely enclosed within guidewire tube 114 regardless of how far catheter 110 has been introduced.

Collapsible guidewire tube 114 may have various constructions. In an exemplary embodiment, illustrated in FIGS. 7A-7C, the collapsible portion 140 of guidewire tube 114 has an accordion-like structure, with walls 142 having a zig-zag cross-section. Collapsible portion 140 comprises a series of conical or dome shaped segments 144 interconnected by hinges 146 that allow the segments to pivot toward and away from each other as guidewire tube 114 is collapsed or extended. In some embodiments, the conical or dome-shaped segments may be configured to nest within one another in the collapsed configuration. Optionally, an additional support tube (not illustrated) may be disposed within guidewire tube 114 extending from its proximal end distally through a portion of the guidewire tube, e.g. 10-30 cm, to keep the guidewire lumen open so that guidewire GW slides smoothly as guidewire tube 114 is collapsed.

Figure 7A:
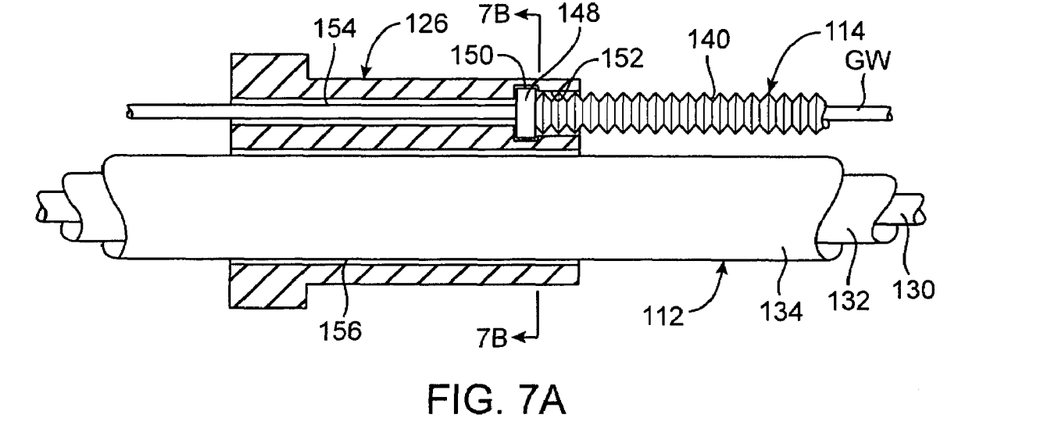
FIG. 7A is a side cross-section of a collar in the stent delivery catheter of FIG. 6.
Figure 7B:
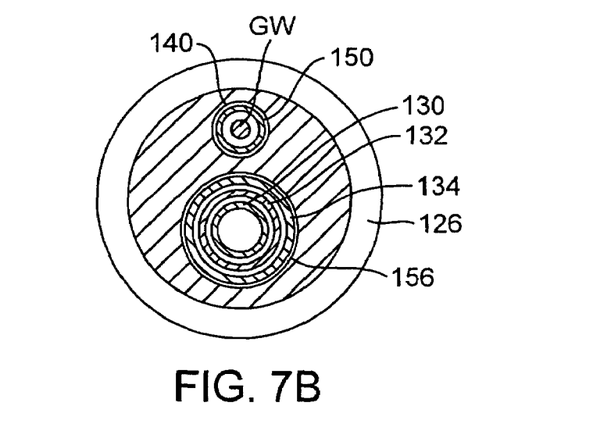
FIG. 7B is a transverse cross-section of the collar of FIG. 7A.

At its proximal end, guidewire tube 114 has a flange 148 of larger diameter that is disposed within a cylindrical chamber 150 in collar 126. A shoulder 152 retains flange 148 within chamber 150. Preferably, flange 148 fits snugly within chamber 150 to provide a hemostatic seal. A first channel 154 through collar 126 is aligned with chamber 150 and permits the passage of guidewire GW through the collar. A second channel 156 is configured to slidably receive catheter body 112, preferably with a fit tight enough to resist leakage of blood. Optionally, an elastomeric hemostatic seal may be provided in either or both of channels 154, 156.

The methods of using the interventional devices of the invention will now be described. While the methods will be described in the context of delivering stents into the coronary arteries, it should be understood that the invention will have utility in performing various diagnostic and treatment procedures in other regions including in peripheral arteries such as the femoral, iliac, and carotid arteries, veins and vein grafts, blood vessels of the brain, organs such as the heart, liver, and kidneys, biliary vessels, intestinal and urinary vessels and organs, lungs, genital organs, and other regions. In addition to stent delivery catheters, the principles of the invention may be applied to various other types of devices including those for angioplasty, drug delivery, delivery of embolic devices, repair of aneurisms, RF mapping and ablation, treatment of atrial fibrillation, heart valve repair and replacement, vascular occlusion, valvuloplasty, intravascular ultrasound, endoscopic visualization, delivery of implantable devices, defect repair, and other purposes.

Referring to the embodiment of FIG. 1, a vascular access site is first selected in a peripheral vessel such as a femoral artery. An introducer is first placed into the vessel throught a puncture, incision or other penetration and a first, larger guidewire is placed through the introducer into the aorta. A guiding catheter is then placed through the introducer over the guidewire, advanced over the aortic arch and into the ostium of the left or right coronary artery. The first guidewire is withdrawn. The guiding catheter will have a rotating hemostasis valve (RHV) on its proximal end that facilitates the introduction of devices while maintaining a seal against the leakage of blood from the vessel. A second smaller guidewire GW is next inserted into the vessel through the RHV, advanced through the guiding catheter into the target coronary artery, and positioned across the stenotic lesion to be treated. The proximal end of guidewire GW is threaded through the guidewire tube 14 on delivery catheter 10. Delivery catheter 10 is advanced over the guidewire into the guiding catheter and collar 26 is inserted into the RHV, which is then tightened to clamp collar 26 in place and seal around its periphery. On the proximal side of collar 26, guidewire GW is disposed outside of guidewire lumen 14 and available for the physician to hold as delivery catheter 10 is advanced over the guidewire into the target vessel. As delivery catheter 10 is advanced distally relative to collar 26, wire guide 80 automatically inserts guidewire GW into guidewire tube 14 through slit 15 so that inside the vessel, guidewire GW is fully enclosed within guidewire tube 14.

Delivery catheter 10 is positioned under fluoroscopic visualization such that the distal end of balloon 20 is even with or just beyond the distal end of the target lesion. Sheath 34 is retracted relative to balloon 20, exposing a desired portion of balloon 20. Initially, pusher 32 may be in "unlocked" mode wherein it moves proximally with sheath 34, allowing stent segments 24 to slide off of the exposed portion of balloon 20. Balloon 20 is then inflated to predilate the lesion. Balloon 20 is then deflated and retracted into sheath 34, and the device is repositioned within the target lesion. Sheath 34 is again retracted, this time with pusher 32 in "locked" mode so as to maintain stent segments 24 in position on balloon 20. Sheath 34 is retracted to expose the desired number of stents corresponding to the length of the lesion being treated. Balloon 20 is inflated to expand stent segments 24 into engagement with the vessel wall. The device may then be repositioned at a different lesion, and the process repeated.

When delivery catheter 10 is withdrawn from the vessel, because wire guide 80 automatically removes guidewire GW from guidewire tube 14, the guidewire is continuously exposed outside the catheter and available for the physician to manipulate at close proximity to the vascular penetration. Advantageously, if delivery catheter 10 is to be exchanged with another catheter, the physician can remove the first catheter from the guidewire and replace it with a second catheter without having to move away from the patient or rely upon the help of an assistant to hold the proximal end of the guidewire.

Figure 7C:
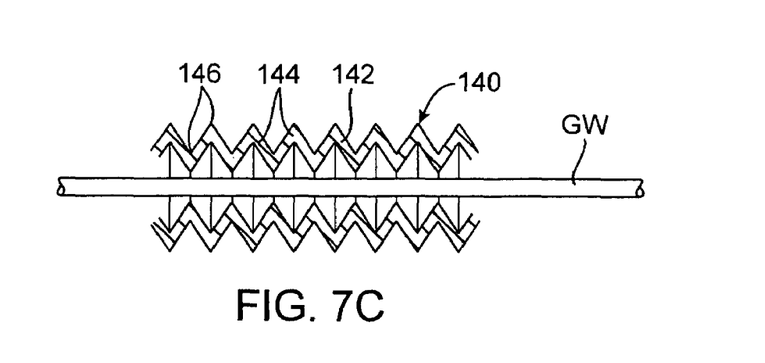
FIG. 7C is a side cross-section of a guidewire tube in the stent delivery catheter of FIG. 6.

From the operator's point of view, the embodiment of FIGS. 6-7 works much the same as that of FIG. 1. Delivery catheter 110 is introduced and operated as just described, the primary difference being that guidewire tube 114 is initially in a collapsed configuration outside the body when guidewire GW is first inserted through it. Guidewire lumen 114 then automatically extends from a collapsed length to an extended length as delivery catheter 110 is advanced to the treatment site. When catheter 110 is withdrawn from the vessel, guidewire tube 114 automatically collapses to a shorter length. Again, outside the body, guidewire GW always remains exposed outside the catheter and available for manipulation by the physician proximal to collar 26.

While the above is a complete description of the preferred embodiments of the invention, various alternatives, modifications, substitutions, equivalents, and additions are possible without departing from the scope thereof, which is defined by the claims.

What is claimed is:

1. An interventional device for introduction through a vascular penetration to a treatment site in a vessel comprising:
   a catheter shaft having a proximal extremity, a distal extremity and an interventional element coupled to the distal extremity;
   a guidewire tube having a proximal end, a distal end and a guidewire lumen therebetween configured to slidably receive a guidewire, the distal end being coupled to the distal extremity of the catheter shaft and the proximal end being separate from the catheter shaft; and
   a collar having a distal portion with a distal end positionable in the vascular penetration and a proximal portion adapted to remain outside the vascular penetration, the collar having a first longitudinal passageway configured to slidably receive the proximal extremity of the catheter shaft without substantial leakage of blood therethrough, and a second longitudinal passageway configured to slidably receive the proximal end of the guidewire tube without substantial leakage of blood therethrough, wherein the first passageway is discrete from the second passageway from the distal end through at least part of the proximal portion, and
   wherein the proximal extremity of the catheter shaft and the guidewire tube each have a length sufficient to extend to the vascular penetration when the interventional device is positioned at the treatment site.

2. The interventional device of claim 1 wherein the collar is positionable through a hemostatic device in the vascular penetration, the collar having an exterior surface configured to seal within the hemostatic device.

3. The interventional device of claim 1 wherein the collar comprises a seal in communication with the at least one passage for inhibiting leakage of blood around the proximal extremity.

4. The interventional device of claim 1 wherein the guidewire tube comprises a slit disposed longitudinally therein from a distal point less than about 50 cm from the distal end to a proximal point at least about one-half the length of the guidewire tube from the distal end.

5. The interventional device of claim 4 wherein the proximal point is within about 20 cm from the proximal end.

6. The interventional device of claim 4 wherein the proximal point is at the proximal end.

7. The interventional device of claim 4 further comprising a wire guide positionable through the slit and operative upon the guidewire such that the guidewire is disposed in the guidewire lumen distal to the wire guide and disposed outside the guidewire lumen proximal to the wire guide.

8. The interventional device of claim 7 wherein the wire guide is coupled to the collar.

9. The interventional device of claim 7 wherein the wire guide comprises a distal opening, a proximal opening, and a guide passage therebetween, the distal opening being aligned with the guidewire lumen and the proximal opening being outside the guidewire tube when the wire guide is positioned through the slit.

10. The interventional device of claim 7 wherein the wire guide comprises a rounded or tapered distal edge configured to spread the slit in the guidewire tube.

11. The interventional device of claim 1 wherein the guidewire tube has a length of at least about 100 cm.

12. The interventional device of claim 1 wherein the guidewire tube is collapsible from an extended length to a collapsed length.

13. The interventional device of claim 12 wherein the guidewire tube has an accordion-like wall.

14. The interventional device of claim 12 wherein the guidewire tube comprises a series of generally conical segments connected by hinges, adjacent conical segments being pivotable toward and away from each other about the hinges.

15. The interventional device of claim 12 wherein the guidewire tube has a wall with a zig-zag cross-section.

16. The interventional device of claim 12 wherein the collapsed length is less than about 50% of the extended length.

17. The interventional device of claim 1 wherein the interventional element comprises a stent.

18. The interventional device of claim 17 wherein the interventional element comprises a plurality of stent segments.

19. The interventional device of claim 18 further comprising a sheath slidably disposed over the stent segments.

20. The interventional device of claim 19 wherein the sheath may be selectively positioned to deploy a first selected number of stent segments from the catheter shaft while retaining a second selected number of stent segments on the catheter shaft.

21. The interventional device of claim 19, wherein the sheath comprises an annular ridge disposed near a distal end of the sheath and adapted to engage at least one of the plurality of stent segments.

22. The interventional device of claim 18, further comprising a pusher member slidably disposed over the catheter shaft, the pusher adapted to prevent proximal movement of the plurality of stent segments.

23. The interventional device of claim 1 wherein the interventional element comprises a balloon.

24. The interventional device of claim 23 further comprising a sheath slidably disposed over the balloon.

25. The interventional device of claim 24 wherein the sheath may be selectively positioned to expand a first portion of the balloon while constraining a second portion of the balloon.

26. The interventional device of claim 1 wherein the guidewire tube couples with the catheter shaft proximal to the interventional element and extends to a point distal to the interventional element.

27. The interventional device of claim 1, further comprising a therapeutic agent disposed on the interventional element.

28. The interventional device of claim 27, wherein the therapeutic agent reduces restenosis.

29. The interventional device of claim 1, further comprising a biodegradable polymeric coating disposed on the interventional element.

* * * * *